15

(12) United States Patent
Prescott et al.

(10) Patent No.: US 9,717,590 B2
(45) Date of Patent: Aug. 1, 2017

(54) ADJUSTABLE LENGTH OSSICULAR PROSTHESIS WITH LOW PROFILE RESILIENT JOINT

(71) Applicant: Enteroptyx, Inc., Memphis, TN (US)

(72) Inventors: Anthony D. Prescott, Arlington, TN (US); Patrick Ireland, Cordova, TN (US)

(73) Assignee: ENTEROPTYX, INC., Memphis, TN (US)

( * ) Notice: Subject to any disclaimer, the term of this patent is extended or adjusted under 35 U.S.C. 154(b) by 83 days.

(21) Appl. No.: 14/865,655

(22) Filed: Sep. 25, 2015

(65) Prior Publication Data

US 2017/0086968 A1    Mar. 30, 2017

(51) Int. Cl.
*A61F 2/18* (2006.01)
*A61F 11/00* (2006.01)

(52) U.S. Cl.
CPC ............... *A61F 2/18* (2013.01); *A61F 11/00* (2013.01); *A61F 2002/183* (2013.01)

(58) Field of Classification Search
None
See application file for complete search history.

(56) References Cited

U.S. PATENT DOCUMENTS

| 5,554,188 | A | 9/1996 | Prescott |
| 6,168,625 | B1 | 1/2001 | Prescott |
| 6,387,128 | B1 | 5/2002 | Kurz et al. |
| 6,432,139 | B1 | 8/2002 | Elies et al. |
| 6,482,144 | B1 | 11/2002 | Muller |
| 6,942,696 | B1 | 9/2005 | White et al. |
| 7,553,328 | B2 | 6/2009 | Steinhardt et al. |
| RE40,853 | E | 7/2009 | White et al. |
| 8,192,489 | B2 | 6/2012 | Edwards |
| 8,518,112 | B2 | 8/2013 | Lenarz et al. |
| 8,936,637 | B2 | 1/2015 | Steinhardt et al. |

(Continued)

FOREIGN PATENT DOCUMENTS

EP    2441415    4/2012

OTHER PUBLICATIONS

Medtronic ENT International Product Catalog 2013-2014 (Aug. 2012) pp. i-7, 99-136.

(Continued)

*Primary Examiner* — Katrina Stransky
*Assistant Examiner* — Wade P Schutte
(74) *Attorney, Agent, or Firm* — Gordon & Jacobson, P.C.

(57) ABSTRACT

An ossicular prosthesis is adjustable in length and temporarily and resiliently adjustable in angular orientation. The prosthesis includes a head for contacting a tympanic membrane, and a resilient sleeve is mounted within the head. An elongate shaft extends through the sleeve, and includes a distal end adapted to engage a footplate or stapes. The sleeve forms a resilient joint that allows the shaft to undergo an angular motion relative to the sleeve when subject to a non-axial force, and then subsequently return to its original position after the force is removed. The sleeve may also be longitudinally displaceable within the head of the prosthesis such that the shaft can undergo a damped linear motion. Also as a result of the arrangement of the sleeve, the prosthesis is adjustable to a very short length.

20 Claims, 6 Drawing Sheets

(56) References Cited

U.S. PATENT DOCUMENTS

2001/0005475 A1*  6/2001  Frigg ................ A61B 17/0401
                                                          411/501
2007/0083263 A1*  4/2007  Steinhardt ................ A61F 2/18
                                                          623/10
2010/0262236 A1  10/2010  Steinhardt et al.
2012/0283827 A1  11/2012  Mendius et al.

OTHER PUBLICATIONS

New Total Ossicular Replacement Prostheses With a Resilient Joint: Experimental Data From Human Temporal Bones, Irina Arechvo et al., Otology & Neurology vol. 33, No. 1, pp. 60-66, 2012.
Olympus, Sound Innovations, Otologic Solutions, Product Catalog, 2009.

* cited by examiner

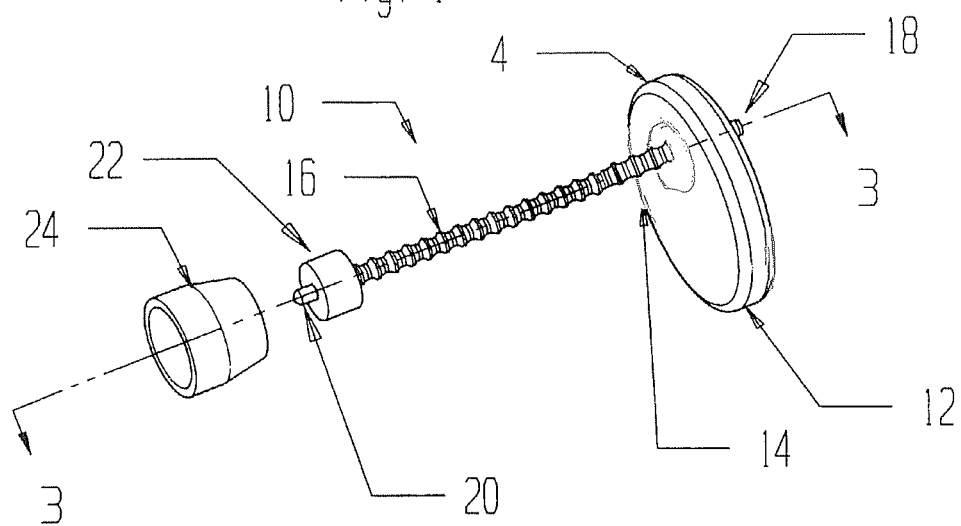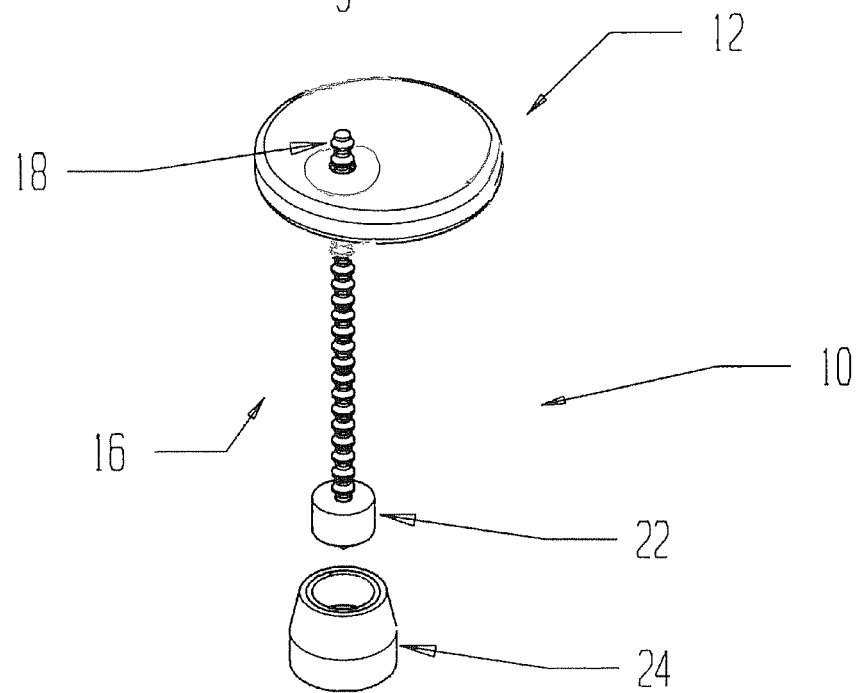

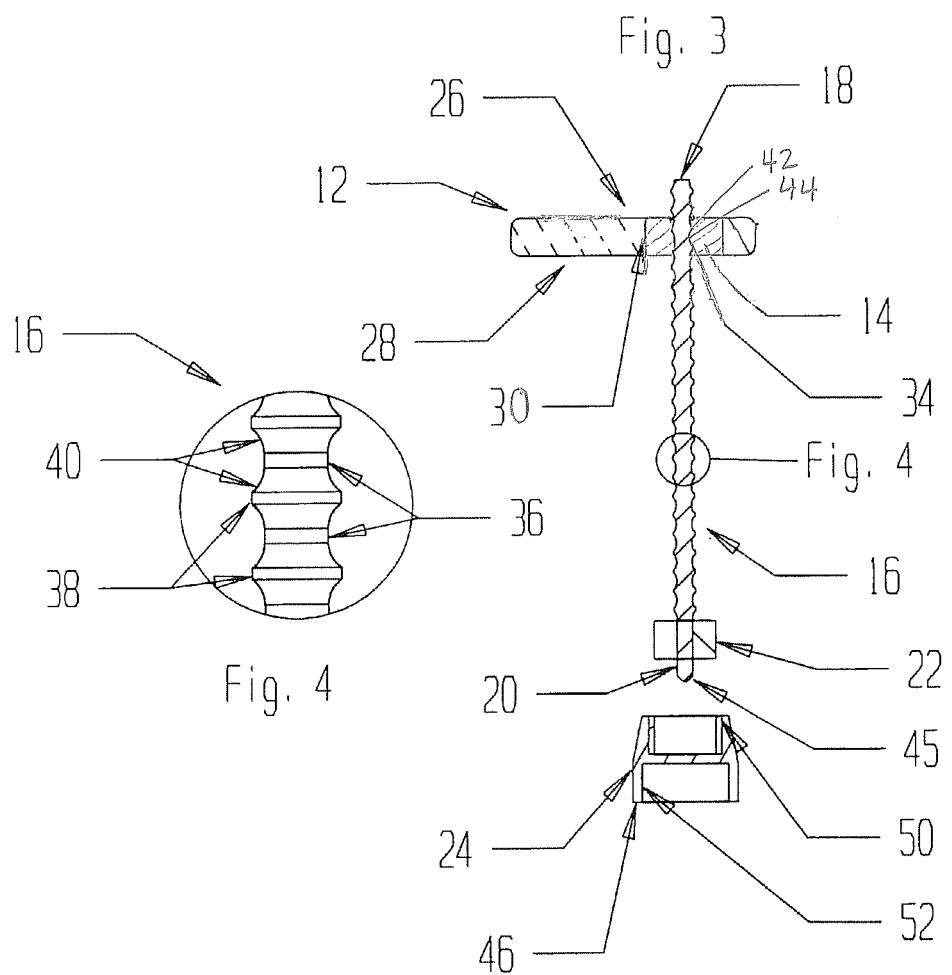

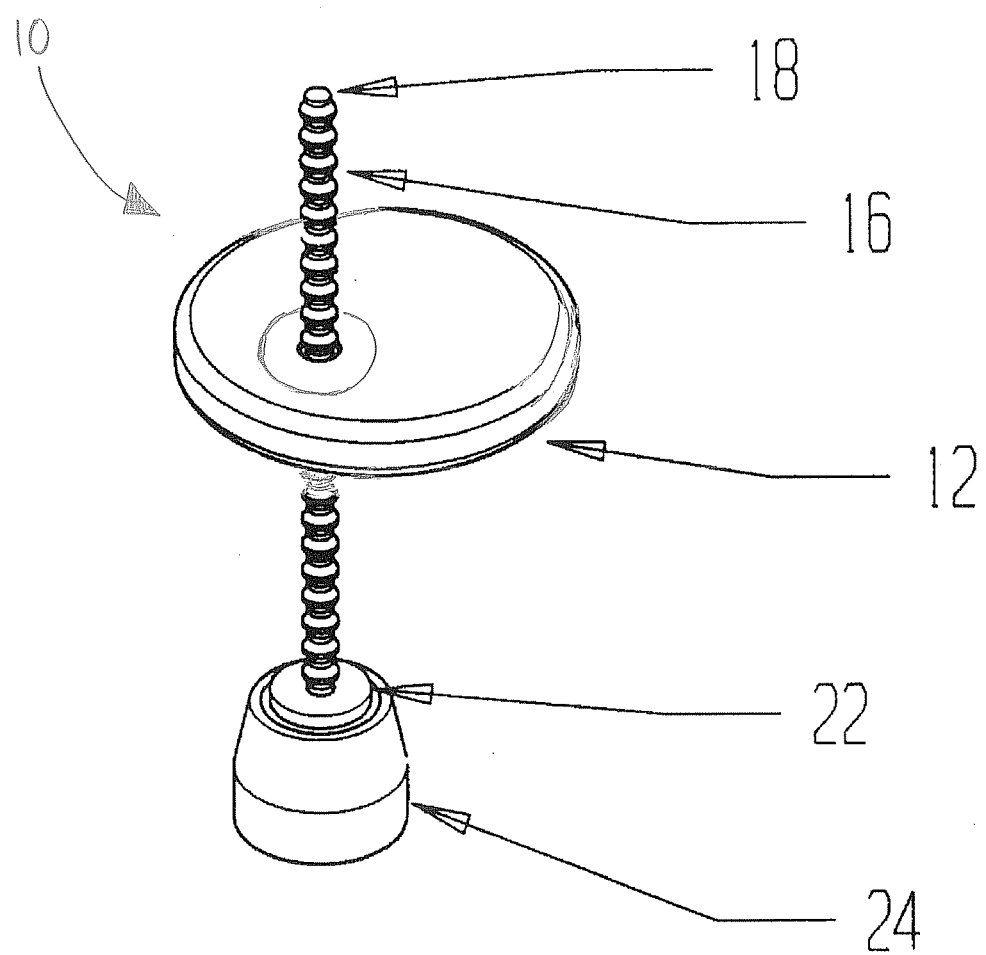

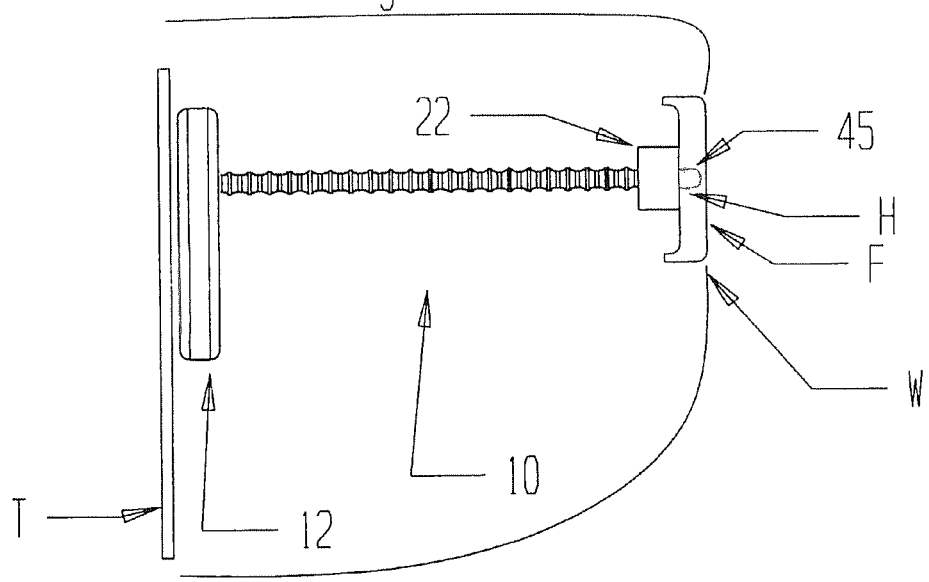
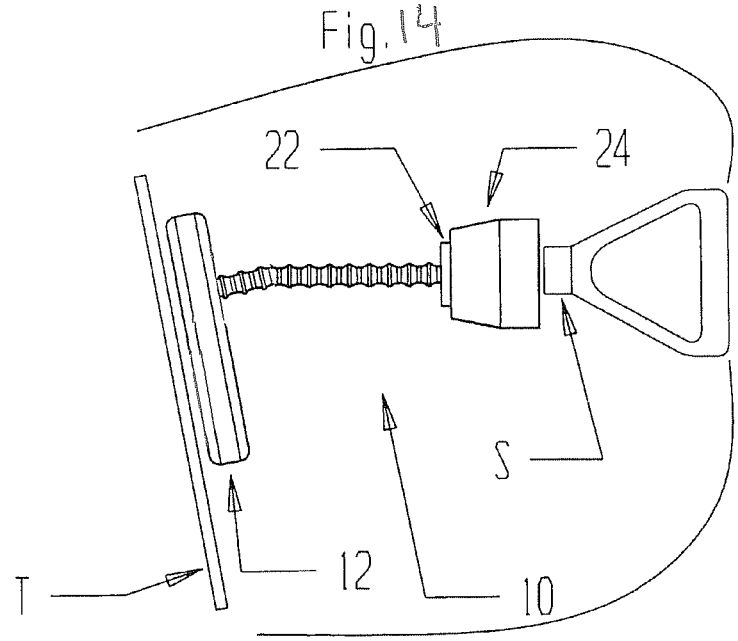

ADJUSTABLE LENGTH OSSICULAR PROSTHESIS WITH LOW PROFILE RESILIENT JOINT

BACKGROUND OF THE INVENTION

1. Field of the Invention

The disclosure relates to an ossicular prosthesis used for total replacement and reconstruction of the ossicular chain. More particularly, the disclosure relates to an adjustable length ossicular prosthesis.

2. State of the Art

Due to disease, trauma, or congenital malformation, the ossicles of the middle ear are sometime damaged. If this damage results in a discontinuity of bone between the tympanic membrane and the oval window, no sound conducts and hearing loss results. Some or all of these ossicles can be replaced with a small prosthesis. The material of choice for many years has been and, for some surgeons, continues to be the patient's own bone. Usually, the incus body will be harvested and reshaped into a strut that bridges whatever gap exists between the tympanic membrane and the oval window. Although this is an effective method of reconstruction, the time required to harvest and sculpt the incus bone into a usable prosthesis has led to the development of synthetic replacements.

Plastic prostheses used for reconstruction of the ossicular chain have been used for some time. A total prosthesis is generally shaped like a nail or tack and replaces all of the ossicles (malleus, incus and stapes) of the middle ear. A partial prosthesis replaces the malleus and the incus. This prosthesis is similar in shape, but has a hollow cylinder for the reduced portion of the prosthesis. The hollow cylinder fits over the head of the stapes. Plastic prostheses generally require a disc of cartilage be placed between the head of the implant and the tympanic membrane. These discs are harvested during surgery. The disc prevents the implant, in most cases, from eroding the tympanic membrane and becoming dislodged over time "extruding".

Subsequent developments have provided movable joints to allow angular adjustment or bendable wire cores. Such joints allow the orientation of a implant to be fixed or set at the time of implantation to match the anatomy.

For each type of ossicular prosthesis, several lengths have generally been provided given the natural differences in anatomical distances between middle ear structures in different patients. This required that a device company manufacture, and that a surgeon (or medical facility) inventory, various sized prosthesis to accommodate the variations in dimensions across the anatomy of patients.

In response, co-owned U.S. Pat. No. RE40,853 discloses an adjustable length prosthesis for ossicular replacement or reconstruction. The disclosed prosthesis is sold by Grace Medical under the trademark ALTO. The ALTO prosthesis includes a head for contacting a tympanic membrane, with the head having a through opening. An elastomeric sleeve is mounted beneath the head at the through opening. The elastomeric sleeve includes a through opening coaxial with the head through opening. An elongate shaft has a near end extending through the sleeve through opening and then the head throughbore. The elastomeric sleeve throughbore is adapted to grip the shaft under static conditions but permit the shaft to move axially to adjust shaft length during the implant procedure. The distal end of the shaft includes structure for contacting a footplate or stapes when implanted in a human ear. The shaft is plastically bendable to accommodate angulation for better anatomical fit. The shaft is received in the head and trimmable with a scissors or scalpel to adjust the length of the prosthesis.

While the ALTO prosthesis works well, the combination of the head and flexible sleeve limit the amount of lengthwise adjustment permissible to the prosthesis prior to implant. In addition, it has been identified that due to ambient or dynamic changes in pressure within the middle ear after implantation, e.g., by sneezing or high sound pressure levels (SPL) caused by an intense noise, the distance and orientation between prosthesis coupling points can temporarily change. This situation may result in dislodgement of the prosthesis or otherwise lead to poor sound conduction along the ossicular chain.

Further, the construction of the ALTO restricts the minimum length to which the prosthesis can be adjusted. For patients with small anatomical spacing between the tympanic membrane and footplate or stapes, such restriction can be a limitation on use of the ALTO prosthesis.

SUMMARY OF THE INVENTION

In accordance with the invention there is disclosed an ossicular prosthesis which is adjustable in length and temporarily and resiliently adjustable in angular orientation. Broadly, the adjustable length ossicular prosthesis includes a head for contacting a tympanic membrane when implanted in a human ear. The head includes a through opening with a first diameter. A flexible sleeve is mounted within the head at the through opening, and includes a throughbore with a smaller diameter than the first diameter. An elongate shaft has a near end and a distal end. The near end extends through the sleeve throughbore. The shaft diameter and sleeve throughbore are sized to each other such that the sleeve grips the shaft under static conditions but also permit the shaft to be moved axially therethrough to adjust the shaft length between the head and the distal end of the shaft. The shaft and sleeve throughbore preferably have corresponding structure that allows incremental discrete displacement relative to each other and subsequent retention. The distal end of the shaft includes structure adapted to engage a footplate or stapes when implanted in a human ear.

In accord with one aspect of the prosthesis, the flexible sleeve is formed of a resilient material, such as a silicone, and forms a resilient joint having an upper and lower profile substantially similar, and preferably coplanar, to upper and lower surfaces of head of the prosthesis. The resilient joint allows the shaft to undergo an angular motion relative to the head when the shaft is subject to a non-axial force, and subsequently return to its original position after the force is removed. The angular motion is predicated on the resilient properties of the sleeve and its position relative to and within the head, rather than a ball and socket structure.

In accord with another preferred aspect of the prosthesis, the sleeve is longitudinally displaceable within the head of the prosthesis such that the shaft can undergo a damped linear motion. The sleeve is in the form of a grommet having a central tube portion bounded by upper and lower shoulder stops. The central tube portion has a length longer than the thickness of the head surrounding the sleeve such that it can be linearly displaced relative to the head. The flexible and resilient sleeve provides for cushioned displacement of the grommet within the head when the head and distal end of the shaft are subject to a linear displacement force.

It is a further feature of the invention that the shaft is defined by alternating enlarged portions and reduced portions and the sleeve expands as the enlarged portions pass through it and contract as the reduced portions pass through.

This provides a slip lock mechanism. The sleeve is preferably size to accommodate two adjacent enlarged portions along the shaft to provide stable angular retention when not subject to resilient angular displacement.

It is an additional feature of the invention that after the prosthesis has been adjusted to length by displacement of the shaft through the sleeve, the near end of the shaft protruding through the head can be trimmed. By positioning the resilient sleeve within the head of the prosthesis, the prosthesis can be adjusted to a shorter length than permitted by previous adjustable length prostheses that included a sleeve positioned below the head and between the head and distal end of the shaft. By way of example, the prosthesis can be adjusted to a minimum length of 0.75 mm between the head and distal end of the shaft.

BRIEF DESCRIPTION OF THE DRAWING

FIG. 1 is a perspective view of an adjustable length ossicular prosthesis according to the invention viewed looking in an outer direction;

FIG. 2 is a perspective view of the prosthesis of FIG. 1 viewed looking in an inner direction;

FIG. 3 is a partial sectional view taken along the line 3-3 of FIG. 1;

FIG. 4 is a detailed view of an encircled portion of a shaft of FIG. 3;

FIG. 10 is a perspective view of the prosthesis of FIG. 1 with its length adjusted for a partial reconstruction;

FIG. 13 is an elevation view illustrating the prosthesis of FIG. 1 in a human ear when used for total reconstruction; and FIG. 14 is an elevation view illustrating the prosthesis of FIG. 1 in a human ear when used for partial reconstruction.

DETAILED DESCRIPTION OF THE INVENTION

Figure 5:
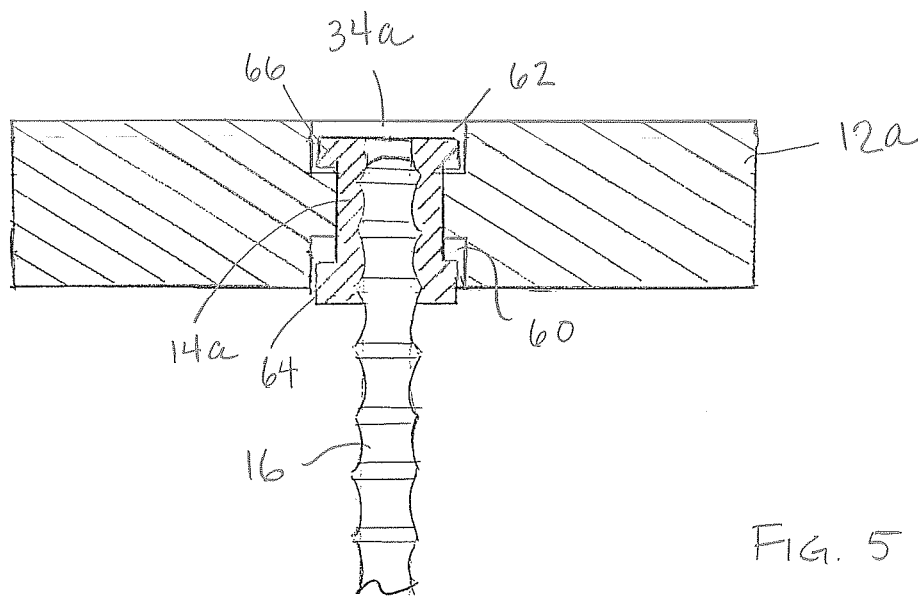
FIG. 5 is an enlarged partial section view of an alternative embodiment of the prosthesis, with the shaft and sleeve in a first displacement relative to the head of the prosthesis.

Referring to FIGS. 1 and 2, an adjustable length ossicular prosthesis 10 according to the invention is illustrated. In accordance with the invention, the prosthesis 10 can be selectively used for total repair or replacement, as discussed below with respect to FIG. 13, or partial repair or replacement, as discussed below with respect to FIG. 14.

The prosthesis 10 includes an enlarged head 12 for contacting a tympanic membrane when implanted in a human ear. According to a preferred aspect of the prosthesis, a flexible sleeve 14 is mounted within the head 12. An elongate shaft 16 has a proximal or outer end 18 and a distal or inner end 20. As used herein, the relative terms inner and outer, and proximal and distal relate to relative position of the prosthesis 10 when placed in a human ear for its intended operation. The shaft 16 extends from within the sleeve 14 to a smaller middle ear engaging structure, such as a smaller second head 22. The smaller head 22 is selectively mounted to a cylinder 24 for partial replacement or reconstruction.

The enlarged head 12 is generally a circular or ovate disc. As is apparent to those skilled in the art, the head 12 can be designed using many different shapes and sizes adapted to fit different circumstances. The head may be generally a filled solid disc, or some other suitably structural form such as round frame with spokes. The head 12 is preferably titanium, but can alternatively or additionally comprise one or more of a ceramic material, such as hydroxylapatite, a polymer, a bioglass, or artificial or even natural bone. The enlarged head 12 is of a shape adapted to contact the tympanic membrane or an ossicle in a human ear. The size of the head 12 is in the range of 2.5 mm to 5.0 mm diameter and 0.5 mm to 2.0 mm thickness.

Referring also to FIG. 3, the head 12 includes an outer surface 26 adapted to contact the tympanic membrane and an inner surface 28, and has a thickness extending therebetween. The head 12 includes a through opening 30, optionally of a constant diameter, extending completely through the thickness of the head. The through opening 30 may be located off-center (as shown in FIGS. 1-3) or through the center of the head (as shown, e.g., in FIGS. 5-9).

The flexible sleeve 14 comprises a resilient disc sized to be received in the through opening 30 of the head 12. The sleeve includes a throughbore 34. The sleeve 14 is preferably made of resilient silicone. Alternatively, another silastic material or resilient material can be used in addition to or in place of silicone. In an embodiment, the sleeve 14 is a disc flush mounted with the outer and inner surfaces 26, 28 of the head such that sleeve 14 and throughbore 34 are exposed at both the outer and inner surfaces 26, 28 of the head 12. The sleeve 14 can be mechanically attached to the head 12 by being directly molded into the through opening 30 of the head 12, by mechanical coupling (discussed below with respect to alternative sleeve 14a) or by other suitable means.

The shaft 16 is formed of a preferably malleable material such as titanium to be bendable. The shaft 16 is adapted to interlock with the sleeve 14. Particularly, as shown in greater detail in FIG. 4, the shaft 16 is defined by a series of alternating enlarged and reduced cross sectional portions. Particularly, the shaft 16 includes reduced portions 36 alternating with enlarged portions 38. The reduced portions 36 are from 0.1 mm to 0.3 mm in diameter and 0.1 mm to 0.3 mm in length. The enlarged portions 38 are from 0.2 mm to 0.5 mm in diameter and from 0.1 mm to 0.3 mm in length. A preferred arrangement is one in which the alternating segments occur in 0.5 mm increments. The enlarged portion 38 and reduced portion 36 are joined by frustoconical portions 40 to aid in length adjustment. While the shaft 16 is described as being bendable, the prosthesis 10 could be provided with a non-bendable shaft as necessary or desired.

The flexible and resilient sleeve 14 is adapted to grip the shaft 16. Particularly, the throughbore 34 is adapted to provide a cross-sectional shape generally similar to that of the shaft 16. The throughbore 34 includes alternating enlarged portions 42 and reduced portions 44. The enlarged portions 42 are of similar size to the shaft enlarged portions 38 and the reduced portions 44 are of a similar size to the shaft reduced portions 36. The axial spacing of the enlarged portions 42 and the reduced portions 44 corresponds to the similar spacing of the shaft enlarged portions 38 and reduced portions 36. The sleeve is preferably size to accommodate two adjacent enlarged portions along the shaft to provide stable angular retention of the shaft when the shaft is not subject to resilient angular displacement, as discussed in more below. The flexible sleeve 14 may be molded directly onto the shaft 16 to form the throughbore 34.

Figure 6:
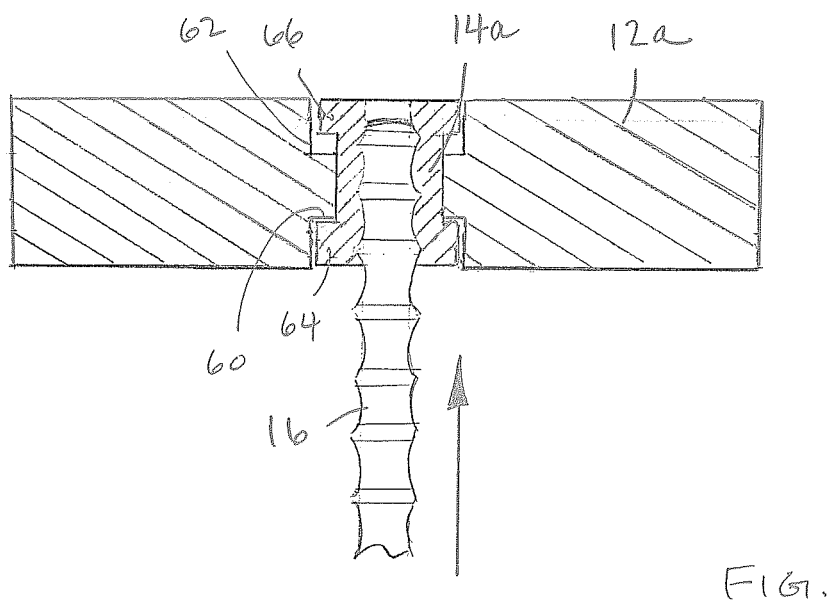
FIG. 6 is a view similar to FIG. 5 with the shaft and sleeve in a second displacement relative to the head of the prosthesis.

Turning to FIGS. 5 and 6, in another embodiment, the through opening 34a of the head 12a includes inner and outer recesses 60, 62 provided at the ends of the through opening 30. The sleeve 14a is bounded at its inner and outer ends by inner and outer shoulders 64, 66, such that the sleeve is generally in the form of a spool. The shoulders 64, 66 are sized to extend into the recesses 60, 62, respectively, and limit and stop displacement of the sleeve 14a there against. The sleeve 14a has a length slightly longer than the thickness of the head (i.e., the inner and outer shoulders 64, 66 are spaced apart more than the thickness of the head 12a between the recesses 60, 62) at the throughbore 34a such that it can be linearly displaced relative to and within the throughbore 34a of the head, with the shoulders 64, 66 functioning as stops against the inner and outer recesses 60, 62 to limit such displacement. In such embodiment, the flexible and resilient sleeve 14a provides for cushioned displacement of the sleeve within the head 12a when the head 12a and shaft 16 are subject to a linear displacement force.

Referring back to FIGS. 1-3, the smaller head 22 at the distal end of the shaft 16 is formed of titanium or another material, preferably similar to the enlarged head 12. It is rigidly coupled to the shaft distal end 20 via unitary construction, a press fit, or using an adhesive. The small head 22 is adapted to contact the oval window or footplate in the human ear when the prosthesis 10 is used for total reconstruction. The cross section of the smaller head may be circular, oval or square and is from 0.4 mm to 1.0 mm in diameter. The length of the small head 22 is from 0.5 mm to 2.0 mm.

Optionally, the distal end 20 of the shaft 14 extends through the smaller head 22 to form an extended sharpened tip 45. This allows surgical fixation of the shaft 16 to the footplate of the stapes by drilling a hole in the footplate and extending the tip 45 into the hole. As a result, the prosthesis 10 can be stabilized on the footplate with a sharpened shaft extension or wire core.

The cylinder 24 for engagement over a stapes S is preferably titanium or any other material described for use with heads 12, 22. The cylinder 24 includes an inner end 46 and a smaller outer end 48. The outer end has a counterbore 50 shown in phantom. The counterbore 50 is of a size and shape corresponding to the smaller head 22 for receiving the same. An enlarged counterbore 52 is positioned at the inner end 46. The cylinder 24 enables the prosthesis 10 to be used for partial reconstruction. Particularly, with the outer counterbore 50 receiving the smaller head 22, the inner end counterbore 52 can engage the head of the stapes. The cylinder outer counterbore 50 may contain a polymeric lining, such as silicone or Teflon® to enhance assembly and hold the cylinder 24 in place during implantation. The cylinder inner counterbore 52 is from 1.0 mm to 2.0 mm in diameter and from 0.5 mm to 2.0 mm in depth. As an alternative, different and/or unitary structure can be formed at, provided directly to, or otherwise coupled to, the distal end of the shaft for engaging the stapes.

Figure 7:
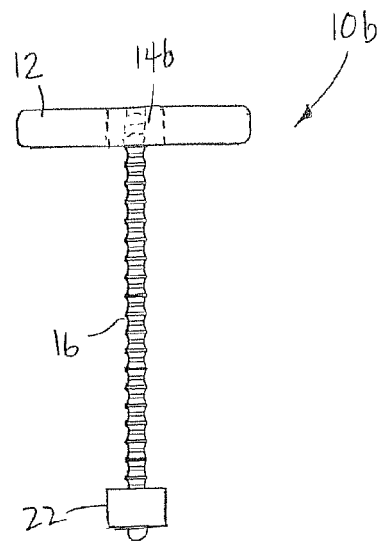
FIG. 7 is a side view of an embodiment of a prosthesis in an at rest configuration.
Figure 8:
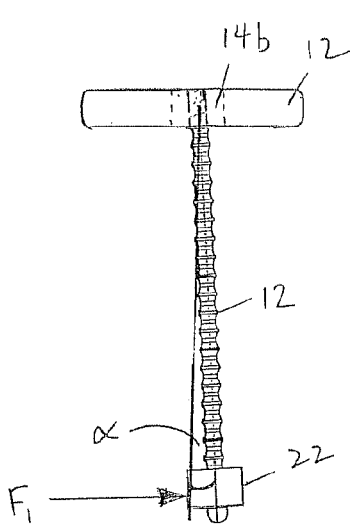
FIG. 8 is a view similar to FIG. 7 with the shaft angularly displaced relative to the head of the prosthesis as a result of a displacement force.
Figure 9:
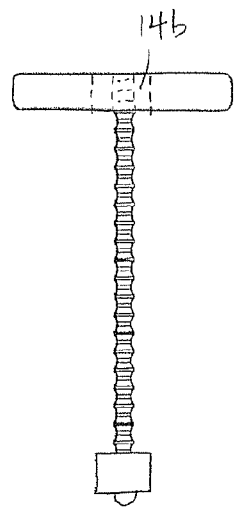
FIG. 9 is a view similar to FIG. 8 after the displacement force has been removed.

Turning now to FIGS. 7-9, in accord with a preferred aspect of the prosthesis 10a, the resilient sleeve mounted within the head is configured and adapted to permit temporary angular displacement of the shaft 16 relative to the head. In FIG. 7, the distal end 22 of the shaft 16, and the proximally located sleeve are shown in a natural, non-displaced configuration. Then, referring to FIG. 8, upon application of lateral force F1 against the shaft 16 while the head 12 is maintained in position, the sleeve 14b underdoes temporary resilient deformation to allow the shaft 16 to under transient angular displacement (angle α) relative to the head 12 to accommodate the lateral force F1. Once the lateral force is removed, the resilient property of the sleeve allows the sleeve 14b the reassume its prior shape, with the shaft against extending axially relative to the through opening (FIG. 9). Thus, while the shaft can be permanently longitudinally displaced relative to the sleeve, the shaft and sleeve are not subject to transient displacement, and not permanent angular displacement, relative to each other.

Referring to FIG. 10, for ossicular replacement or reconstruction, the surgeon can adjust the length of the prosthesis 10 in increments determined by the configuration of the shaft 16. Particularly, in the example discussed above, the surgeon can adjust length in 0.5 mm increments defined by spacing between the reduced portions 36. By applying a compressive force relative to the enlarged head 12 and smaller head 22, the implant is shortened by forcing the shaft 16 outwardly, as illustrated in FIG. 10. The shaft requires not less than a 15 gram force and not more than an 80 gram force for length adjustment. The flexible sleeve 14 accommodates the enlarged portions 38 to pass through the smaller portions 44 of the through opening 34 and resumes retention once the linear displacement force is removed. By adjusting the mechanical properties of the material of the sleeve 14 or changing the ratio of the enlarged portions 38 and reduced portions 36 of the shaft 16, the tightness of the slip lock may be adjusted. The slip lock should be loose enough to allow easy length adjustment by the surgeon, but tight enough to prevent slippage after implantation. The near end 18 of the shaft that extends outwardly from the head 12, see FIG. 10, can then be cut off by the surgeon prior to implantation.

Figure 11:
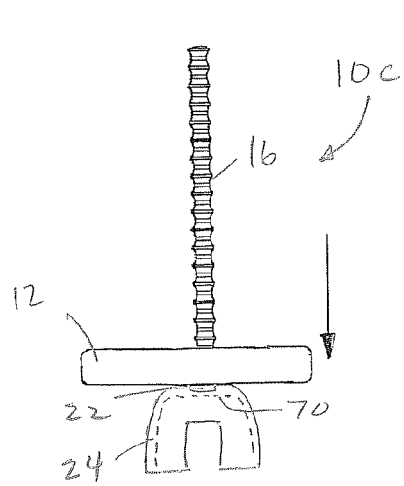
FIG. 11 is a side view of an embodiment of a prosthesis, showing the head longitudinally advanced along the shaft to reduce the length of the prosthesis.
Figure 12:
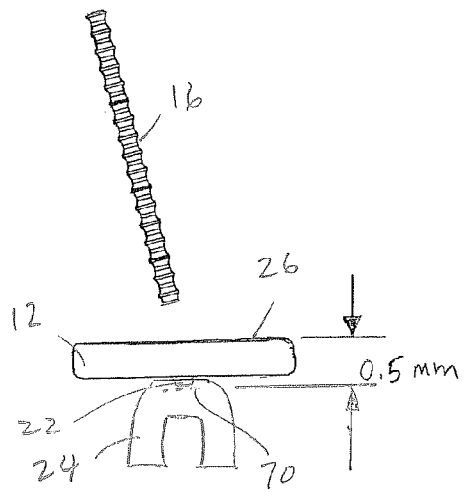
FIG. 12 is a side view of an embodiment of the prosthesis of FIG. 11, in which the protruding portion of the shaft has been removed.

The configuration of the sleeve 14b in the head 12 of the prosthesis 10b permits adjustment of the prosthesis to a very short length, as the sleeve is not interposed between the head and the distal end 22 of the shaft 16. In some implant procedures it is advantageous to have a very short prosthesis to accommodate closely spaced middle ear structures, for example, between a tympanic membrane and a stapes head. Referring to FIGS. 11 and 12, by way of example, the head 12 can be advanced distally relative to the shaft 16 (or the shaft proximally up through the head) all the way until the head is in contact with (or substantially contacts) the a stapes cup 24 or other ossicular engagement structure at the distal end 22 of the shaft. In fact, the prosthesis 10c can be adjusted to a total length of no more than 0.5 mm (between the outer surface 26 of the head and the opposite inner surface 70 of the cup 24), and the protruding portion of the shaft 16 can then be cut off flush with the outer surface 26 of the head 12.

Although the sleeve 14 and shaft 16 are illustrated having alternating reduced and enlarged cross-sections, such structure is not required in accordance with the teachings of the invention. In fact, one of the two elements could have such a cross-section with the other having a fixed cylindrical cross-section, provided suitable gripping is evident. Moreover, both could have fixed cylindrical cross-section with suitable gripping to prevent slippage. Likewise, the shaft 16 could be formed of a coiled spring or helical thread received in a helical through opening of the sleeve 14. The shaft 16 would then be screwed in or out. This design could be used to protect the cochlea from pressure trauma.

Referring to FIG. 13, the prosthesis 10 is illustrated fitted in a human ear for total reconstruction or replacement. Particularly, the enlarged head 12 contacts the tympanic membrane T. The smaller head 22 contacts the footplate F of the oval window W. The shaft tip 45 is shown, in phantom, in a hole H drilled by the surgeon in the footplate F.

Referring to FIG. 14, the prosthesis 10 is illustrated fitted in a human ear for partial reconstruction or replacement. Particularly, the enlarged head 12 contacts the tympanic membrane T. The smaller head 22 is mounted to the cylinder 24 which receives the head of the stapes S.

Thus, in accordance with the invention there is provided an ossicular prosthesis that provides simple length adjustment to even very short lengths, dampening under longitudinal force, and temporary and resilient angular orientation.

There have been described and illustrated herein embodiments of an ossicular prosthesis. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other suitable materials can be used as well. In addition, while particular structures for engaging the middle ear anatomy (e.g., large head, small head, cylinder, etc.) have been disclosed, it will be understood that other suitable structures can be used. It will therefore be appreciated by those skilled in the art that yet other modifications could be made to the provided invention without deviating from its scope as claimed.

What is claimed is:

1. An ossicular prosthesis for implantation entirely within the middle ear, the prosthesis comprising:
   a) a head configured to contact a first middle ear anatomy, the head including an outer surface, an inner surface, a through opening extending through the head from the outer surface to the inner surface;
   b) a sleeve retained within the through opening, but axially displaceable within the through opening of the head, the sleeve having a throughbore, the sleeve and throughbore exposed at both the outer and inner surfaces of the head; and
   c) a shaft extending within the sleeve, the shaft having a portion extending within the sleeve and a distal end provided with structure for contacting a second middle ear anatomy,
      wherein a linear force on the shaft relative to the head results in damped linear motion of the sleeve relative to the head.

2. The ossicular prosthesis of claim 1, wherein:
the sleeve includes upper and lower stops that limit travel of the sleeve within the head.

3. The ossicular prosthesis of claim 2, wherein:
the sleeve is comprised of a resilient material.

4. The ossicular prosthesis of claim 1, wherein:
the head is configured to contact the tympanic membrane, and the structure at the distal end of the shaft is configured to engage a stapes or a stapes footplate.

5. The ossicular prosthesis of claim 1, wherein:
the prosthesis may be adjusted to have a length of 0.5 mm between the outer surface of the head and the structure for contacting the second middle ear anatomy.

6. An ossicular prosthesis for implantation entirely within the middle ear, the prosthesis comprising:
   a) a head configured to contact a first middle ear anatomy, the head including an outer surface, an inner surface, a through opening extending through the head from the outer surface to the inner surface;
   b) a resilient sleeve located within the through opening of the head, the sleeve having a throughbore, the sleeve and throughbore exposed at both the outer and inner surfaces of the head; and
   c) a shaft extending within the sleeve, the shaft having a portion extending within the sleeve and a distal end provided with structure for contacting a second middle ear anatomy, wherein the shaft is angularly displaceable relative to the head by resilient deformation of the sleeve.

7. The ossicular prosthesis of claim 6, wherein:
the sleeve is fixed within the head.

8. The ossicular prosthesis of claim 6, wherein:
the sleeve is flush with the inner surface of the head.

9. The ossicular prosthesis of claim 8, wherein:
the sleeve is flush with the outer surface of the head.

10. The ossicular prosthesis of claim 6, wherein:
the shaft defines a plurality of linearly displaced and alternating enlarged and reduced portions, and the throughbore of the sleeve accommodates at least two of the enlarged portions such that the shaft and resilient sleeve are not subject to permanent angular displacement relative to each other.

11. The ossicular prosthesis of claim 6, wherein:
the sleeve is made of silicone or other silastic material.

12. The ossicular prosthesis of claim 6, wherein:
the sleeve is linearly displaceable within the head.

13. The ossicular prosthesis of claim 12, wherein:
the sleeve includes upper and lower stops that limit travel of the sleeve within the head.

14. The ossicular prosthesis of claim 6, wherein:
the shaft defines a plurality of linearly displaced and alternating enlarged and reduced portions, and the throughbore of the sleeve accommodates at least two of the enlarged portions such that the shaft and resilient sleeve are not subject to permanent angular displacement relative to each other.

15. The ossicular prosthesis of claim 14, wherein:
the shaft has an axis, and the enlarged portions have a non-circular cross section orthogonal to the axis of the shaft.

16. The ossicular prosthesis of claim 6, wherein:
the shaft defines a plurality of linearly displaced and alternating enlarged and reduced portions, and the throughbore of the sleeve accommodates at least two of the enlarged portions such that the shaft requires not less than a 15 gram force and not more than an 80 gram force for length adjustment.

17. The ossicular prosthesis of claim 16, wherein:
the shaft has an axis, and the enlarged portions have a non-circular cross section orthogonal to the axis of the shaft.

18. The ossicular prosthesis of claim 6, wherein:
the shaft has an axis, and the enlarged portions have a non-circular cross section orthogonal to the axis of the shaft.

19. The ossicular prosthesis of claim 6, wherein:
the prosthesis may be adjusted to have a length of 0.5 mm between the outer surface of the head and the structure for contacting the second middle ear anatomy.

20. The ossicular prosthesis of claim 6, wherein:
the head is configured to contact the tympanic membrane, and the structure at the distal end of the shaft is configured to engage a stapes or a stapes footplate.

* * * * *